United States Patent [19]
Glase et al.

[11] Patent Number: 5,885,994
[45] Date of Patent: Mar. 23, 1999

[54] TETRAHYDROQUINOXALINE DOPAMINE D4 RECEPTOR ANTAGONISTS

[75] Inventors: Shelly Ann Glase; Suzanne Ross Kesten, both of Ann Arbor, Mich.

[73] Assignee: Warner-Lambert Company, Morris Plains, N.J.

[21] Appl. No.: 35,244

[22] Filed: Mar. 5, 1998

Related U.S. Application Data

[60] Provisional application No. 60/040,209 Mar. 6, 1997.
[51] Int. Cl.$^6$ ........................ A61K 31/495; C07D 241/38
[52] U.S. Cl. ............................................ 514/249; 544/353
[58] Field of Search ............................. 514/249; 544/353

[56] References Cited

U.S. PATENT DOCUMENTS 3,133,069 5/1964 Ash et al. ........................... 544/353 X
4,091,101 5/1978 Lumma, Jr. et al. ............... 544/353 X

*Primary Examiner*—Michael G. Ambrose
*Attorney, Agent, or Firm*—Todd M. Crissey

[57] ABSTRACT

This invention relates to compounds that are antagonists of dopamine D4 receptors having Formula I below

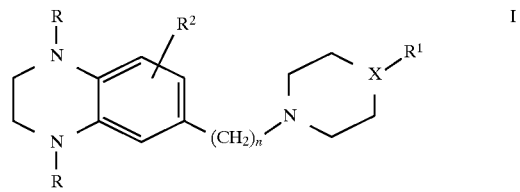

This invention also relates to methods of treating psychosis and schizophrenia using a compound that is an antagonist of dopamine D4 receptors, and to pharmaceutically acceptable compositions that contain a dopamine D4 receptor antagonist.

15 Claims, No Drawings

TETRAHYDROQUINOXALINE DOPAMINE D4 RECEPTOR ANTAGONISTS

This application claims priority of U.S. patent application Ser. No. 60/040,209, filed Mar. 6, 1997.

FIELD OF THE INVENTION

This invention relates to compounds that are antagonists of dopamine D4 receptors, to methods of treating psychosis and schizophrenia using a compound that is an antagonist of dopamine D4 receptors, and to pharmaceutically acceptable compositions that contain a dopamine D4 receptor antagonist.

BACKGROUND OF THE INVENTION

Dopamine is a neurotransmitter that is found in the brains of animals, including humans, and is essential for proper nerve signal transmission. It is well-known that certain compounds block or inhibit the binding of dopamine to dopamine receptors. Such compounds are called dopamine receptor antagonists. It is also well-known that dopamine receptor antagonists are useful in the treatment of schizophrenia and psychosis.

Recently, it has been discovered that more than one type of dopamine receptor exists, and that dopamine receptor antagonists can preferentially inhibit one type of dopamine receptor over another. Two major families of dopamine receptors have been identified and named the D1 and D2 families. In the D2 family, three distinct receptor subtypes have been identified as D2, D3, and D4.

The distribution and concentration of the subtypes of receptors varies in different regions of the brain. D2 subtype receptors are located in both the limbic region of the brain, which is associated with cognition and emotional function, and in the striatum, which is associated with motor effects. D4 receptors are found in higher concentrations in the frontal cortex and limbic regions, which are associated with cognitive and emotional function.

Antipsychotic drugs that are D2 subtype receptor antagonists have been used to treat psychosis and schizophrenia, but have undesirable extrapyramidal side effects and produce tardive dyskinesia. In contrast, D4 receptor antagonists show a lack of extrapyramidal side effects and tardive dyskinesia. Moreover, it has been observed that the levels of dopamine D4 receptors are elevated in schizophrenics.

Thus, it would be useful to have compounds that are selective D4 antagonists for the treatment of psychosis and schizophrenia.

SUMMARY OF THE INVENTION

The present invention provides compounds having the Formula I

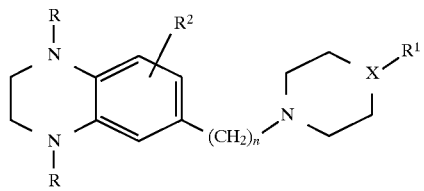

wherein
each R is independently hydrogen or $C_1$–$C_6$ alkyl;
n is 1 to 5;
X is N or CH;
$R^1$ is aryl, substituted aryl, heteroaryl or substituted heteroaryl; and
$R^2$ is halogen, $C_1$–$C_6$ alkyl, —OH, —NO$_2$, —CF$_3$, —CN, —CO$_2$R, or —COR and the pharmaceutically acceptable salts, esters, amides and prodrugs thereof.

In a preferred embodiment of the compounds of Formula I, each R is hydrogen.

In another preferred embodiment of the compounds of Formula I, n is 1.

In another preferred embodiment of the compounds of Formula I, X is N.

In another preferred embodiment of the compounds of Formula I, X is CH.

In another preferred embodiment of the compounds of Formula I, $R^1$ is phenyl or substituted phenyl.

In another preferred embodiment of the compounds of Formula I, $R^1$ is substituted phenyl and the substituents are selected from halogen, $C_1$–$C_6$ alkyl, —CF$_3$, —NO$_2$, —CN, —CO$_2$R, or —COR.

In another preferred embodiment of the compounds of Formula I, $R^1$ is substituted heteroaryl.

In another preferred embodiment of the compounds of Formula I, the substituted heteroaryl is substituted pyridyl.

In another preferred embodiment of the compounds of Formula I, R is hydrogen, n is 1, $R^2$ is hydrogen, X is N and R is aryl, substituted aryl, heteroaryl, or substituted heteroaryl.

In a more preferred embodiment of the compounds of Formula I, the compounds are
6-[4-(3-Chloro-4-methylphenyl)piperazin-1-ylmethyl]1,2,3,4-tetrahydroquinoxaline;
6-[4-(3,4-Dimethylphenyl)piperazin-1-ylmethyl]1,2,3,4-tetrahydroquinoxaline;
6-(4-Phenylpiperazin-1-ylmethyl)1,2,3,4-tetrahydroquinoxaline;
6-[4-(4-Methoxyphenyl)piperazin-1-ylmethyl]1,2,3,4-tetrahydroquinoxaline;
6-[4-(4-Chlorophenyl)piperazin-1-ylmethyl]1,2,3,4-tetrahydroquinoxaline;
6-[4-(4-Fluorophenyl)piperazin-1-ylmethyl]1,2,3,4-tetrahydroquinoxaline;
6-[4-(3,4-Dichlorophenyl)piperazin-1-ylmethyl]1,2,3,4-tetrahydroquinoxaline;
6-(4-p-Tolylpiperazin-1-ylmethyl)1,2,3,4-tetrahydroquinoxaline;
6-(4-m-Tolylpiperazin-1-ylmethyl)1,2,3,4-tetrahydroquinoxaline;
6-[4-(4-Methylpyridin-2-yl)piperazin-1-ylmethyl]1,2,3,4-tetrahydroquinoxaline;
6-[4-(3-Trifluoromethylphenyl)piperazin-1-ylmethyl]1,2,3,4-tetrahydroquinoxaline;
6-(4-o-Tolylpiperazin-1-ylmethyl)1,2,3,4-tetrahydroquinoxaline;
6-[4-(3-Chlorophenyl)piperazin-1-ylmethyl]1,2,3,4-tetrahydroquinoxaline;
6-[4-(2-Chlorophenyl)piperazin-1-ylmethyl]1,2,3,4-tetrahydroquinoxaline; or
6-[4-(3,4-Dimethylphenyl)piperidin-1-ylmethyl]1,2,3,4-tetrahydroquinoxaline.

Also provided by the present invention is a method of treating psychosis, the method comprising administering to a patient having psychosis a therapeutically effective amount of a compound of Formula I.

Also provided by the present invention is a method of treating schizophrenia, the method comprising administering to a patient having schizophrenia a therapeutically effective amount of a compound of Formula I.

Also provided by the present invention is a method of inhibiting dopamine D4 receptors, the method comprising administering to a patient in need of dopamine D4 receptor inhibition an inhibiting amount of a compound of Formula I.

Also provided by the present invention is a pharmaceutically acceptable composition, the composition comprising a compound of Formula I.

DETAILED DESCRIPTION OF THE INVENTION

The present invention provides compounds having the Formula I

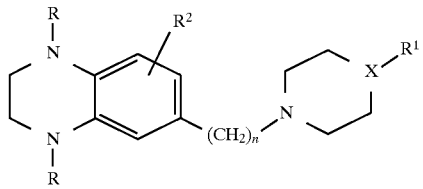

wherein
each R is independently hydrogen or $C_1$–$C_6$ alkyl;
n is 1 to 5;
X is N or CH;
$R^1$ is aryl, substituted aryl, heteroaryl, or substituted heteroaryl; and
$R_2$ is halogen, $C_1$–$C_6$ alkyl, —OH, —NO$_2$, —CF$_3$, —CN, —CO$_2$R, or —COR and the pharmaceutically acceptable salts, esters, amides, and prodrugs thereof.

The term "alkyl" means a straight or branched chain hydrocarbon. Representative examples of alkyl groups are methyl, ethyl, propyl, isopropyl, isobutyl, butyl, tert-butyl, sec-butyl, pentyl, and hexyl.

The term "aryl" means a cyclic aromatic hydrocarbon. Representative examples of aryl groups include phenyl and naphthyl, which can be substituted or unsubstituted. Examples of suitable substituents include halogen, $C_1$–$C_6$ alkyl, hydroxy, $C_1$–$C_6$ alkoxy, —CF$_3$, and sulfonamides.

The term "heteroaryl" means a cyclic hydrocarbon that contains one or more heteroatom. Representative examples of heteroaryl groups are thiazole, thiophene, and pyridine, pyrimidine, quinoline, isoquinoline, and imidazole. The heteroaryl group can be substituted or unsubstituted. Examples of suitable substituents include $C_1$–$C_6$ alkyl, —OH, $C_1$–$C_6$ alkoxy, or halogen.

The term "heteroatom" means an atom other than carbon. Examples of heteroatoms include nitrogen, oxygen, sulfur, and phosphorus.

The term "halogen" means chlorine, fluorine, bromine, and iodine.

The term "sulfonamido" means a group having the structure —SONR$^a$R$^b$, where R$^a$ and R$^b$ are sulfonamido substituents well-known to those skilled in the art such as hydrogen and $C_1$–$C_6$ alkyl.

The symbol "—" means a bond.

The term "patient" includes humans.

A "therapeutically effective amount" is an amount of a compound of the present invention that when administered to a patient ameliorates a symptom of psychosis or schizophrenia. A therapeutically effective amount of a compound of the present invention can be easily determined by one skilled in the art by administering a quantity of a compound to a patient and observing the result. In addition, those skilled in the art are familiar with identifying patients having psychosis and schizophrenia and are readily able to identify patients who suffer from psychosis and schizophrenia.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgement, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively nontoxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium and the like, as well as nontoxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M., et al., "Pharmaceutical Salts," *J. Pharm. Sci.*, 1977;66:1–19 which is incorporated herein by reference).

Examples of pharmaceutically acceptable, nontoxic esters of the compounds of this invention include $C_1$–$C_6$ alkyl esters wherein the alkyl group is a straight or branched chain. Acceptable esters also include $C_1$–$C_6$ cycloalkyl esters as well as arylalkyl esters such as, but not limited to benzyl. $C_1$–$C_6$ alkyl esters are preferred. Esters of the compounds of the present invention may be prepared according to conventional methods.

Examples of pharmaceutically acceptable, nontoxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines the amine may also be in the form of a 5- or 6-membered heterocycle containing one nitrogen atom. Amides derived from ammonia, $C_1$–$C_6$ alkyl primary amines and $C_1$–$C_6$ dialkyl secondary amines are preferred. Amides of the compounds of the invention may be prepared according to conventional methods.

The term "prodrug" refers to compounds that are rapidly transformed in vivo to yield the parent compound of the above formula, for example, by hydrolysis in blood. A thorough discussion is provided in Higuchi T. and Stella V., "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are incorporated herein by reference.

The compounds of the present invention can be administered to a patient alone or as part of a composition that contains other components such as excipients, diluents, and carriers, all of which are well-known in the art. The compositions can be administered to humans and animals either orally, rectally, parenterally (intravenously, intramuscularly or subcutaneously), intracisternally, intravaginally, intraperitoneally, intravesically, locally (powders, ointments or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft- and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well-known in the art. They may contain opacifying agents and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitol or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable nonirritating excipients or carriers such as cocoa butter, polyethyleneglycol, or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The compounds of the present invention can be administered to a patient at dosage levels in the range of about 0.1 to about 2,000 mg per day. For a normal human adult having a body weight of about 70 kg, a dosage in the range of about 0.01 to about 100 mg/kg of body weight per day is preferable. The specific dosage used, however, can vary. For example, the dosage can depended on a numbers of factors including the requirements of the patient, the severity of the condition being treated, and the pharmacological activity of the compound being used. The determination of optimum dosages for a particular patient is well-known to those skilled in the art.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The compounds of the present invention can exist in different stereoisomeric forms by virtue of the presence of asymmetric centers in the compounds. It is contemplated that all stereoisomeric forms of the compounds as well as mixtures thereof, including racemic mixtures, form part of this invention.

The examples shown below illustrate particular embodiments of the invention and are not intended to limit the specification, including the claims, in any manner.

EXAMPLE 1

6-[4-(3-Chloro-4-methylphenyl)piperazin-1-ylmethyl]-1,2,3,4-tetrahydroquinoxaline Step A 1,1'-Carbonyldiimidazole (0.48 g, 3.0 mmol) is added to a suspension of 6-quinoxaline carboxylic acid (0.52 g, 3.0 mmol) in dichloromethane (15 mL) and stirred for 1 hour at room temperature under a nitrogen atmosphere. 1-(3-Chloro, 4-methylphenyl)piperazine (0.63 g, 3.0 mmol) in dichloromethane (5 mL) is added dropwise, and the reaction is stirred for 15 hours at room temperature. The reaction mixture is diluted with dichloromethane (20 mL), washed with 2N NaOH, dried (magnesium sulfate), and concentrated in vacuo. The resulting material is purified by medium pressure liquid chromatography (MPLC) on silica gel eluting with ethyl acetate to give 0.97 g of the amide intermediate as a pale yellow solid; mp 134° C.

Step B

A solution of aluminum chloride (0.268 g, 2.02 mmol) in anhydrous ethyl ether (20 mL) is added dropwise to a suspension of lithium aluminum hydride (0.230 g, 6.04 mmol) in anhydrous tetrahydrofuran (20 mL) at 0° C. and stirred for ½ hour. To this mixture is added dropwise a solution of the amide intermediate from Step A (0.92 g, 2.52 mmol) in anhydrous tetrahydrofuran (20 mL). The suspension is stirred for 2 hours at 0° C., followed by dropwise addition of 2N sodium hydroxide. The mixture is filtered through Celite and concentrated in vacuo. The resulting product is purified by MPLC on silica gel eluting with 2% methanol/dichloromethane to give 0.19 g of the title compound as a white solid; mp 151°–152° C.

Elemental Analysis calculated for $C_{20}H_{25}ClN_4.0.20\ H_2O$: C: 66.63, H: 7.10, N: 15.55. Found: C: 66.65, H: 6.94, N: 15.40.

EXAMPLE 2

6-[4-(3,4-Dimethylphenyl)piperazin-1-ylmethyl]-1,2,3,4-tetrahydroquinoxaline

Step A

A solution of 6-quinoxaline carboxylic acid (0.9 g, 5.14 mmol) and triethylamine (0.75 mL, 5.50 mmol) in dichloromethane (90 mL) is treated with isobutylchloroformate (0.67 mL, 5.14 mmol) and stirred for 2 hours at room temperature under a $N_2$ atmosphere. 1-(3,4-dimethylphenyl) piperazine (0.98 g, 5.14 mmol) is added, and the reaction is stirred for 18 hours at room temperature. The reaction mixture is washed with saturated aqueous $NaHCO_3$, dried (potassium carbonate), and concentrated in vacuo. The resulting material is purified by MPLC on silica gel eluting with 5% isopropyl alcohol in dichloromethane to give 0.97 g of the amide intermediate as a pale yellow solid; mp 93°–94° C.

Step B

A 1M solution of HCl in ethyl ether (12 mL, 12 mmol) is added dropwise to a solution of 1N lithium aluminum hydride in ethyl ether (12 mL, 12 mmol) and tetrahydrofuran (100 mL). After 30 minutes a solution of the amide intermediate from Step A (0.8 g, 2.3 mmol) in tetrahydrofuran (100 mL) is added dropwise over 1 hour and stirred for 18 hours at room temperature under a $N_2$ atmosphere. The reaction is carefully quenched by addition of water and saturated aqueous sodium sulfate, stirred 1 hour, filtered through Celite, and concentrated in vacuo. The residue is partitioned between dichloromethane and saturated aqueous $NaHCO_3$, dried (potassium carbonate), and concentrated in vacuo. The resulting material is triturated with diethyl ether to give 0.55 g of the title compound as a white solid; mp 148°–149° C.

Elemental Analysis calculated for $C_{21}H_{28}N_4.0.20\ H_2O$: C: 74.17, H: 8.42, N: 16.47. Found: C: 74.18, H: 8.61, N: 16.22.

EXAMPLE 3

6-(4-Phenylpiperazin-1-ylmethyl)-1,2,3,4-tetrahydroquinoxaline

Example 3 was prepared according to Example 2 except that in Step A 1-phenylpiperazine is substituted for 1-(3,4-dimethylphenyl)piperazine; mp 124°–126° C.

Elemental Analysis: calculated for $C_{19}H_{24}N_4.0.10\ H_2O$: C: 73.56, H: 7.86, N: 18.06. Found: C: 73.39, H: 8.02, N: 17.93.

EXAMPLE 4

6-[4-(4-Methoxyphenyl)piperazin-1-ylmethyl]-1,2,3,4-tetrahydroquinoxaline

Example 4 was prepared according to Example 2 except that in Step A 1-(4-methoxyphenyl)piperazine is substituted for 1-(3,4-dimethylphenyl)piperazine; mp 169°–171° C.

Elemental Analysis calculated for $C_{20}H_{26}N_4.0.15\ H_2O$: C: 70.41, H: 7.77, N: 16.42. Found: C: 70.40, H: 7.72, N: 16.28.

EXAMPLE 5

6-[4-(4-Chlorophenyl)piperazin-1-ylmethyl]1,2,3,4-tetrahydroquinoxaline

Example 5 was prepared according to Example 2 except that in Step A 1-(4-chlorophenyl)piperazine is substituted for 1-(3,4-dimethylphenyl)piperazine; mp 145°–148° C.

Elemental Analysis calculated for $C_{19}H_{23}ClN_4.0.40\ H_2O$: C: 65.19, H: 6.85, N: 16.00. Found: C: 65.36, H: 6.80, N: 15.47.

EXAMPLE 6

6-[4-(4-Fluorophenyl)piperazin-1-ylmethyl]-1,2,3,4-tetrahydroquinoxaline

Example 6 was prepared according to Example 2 except that in Step A 1-(4-fluorophenyl)piperazine is substituted for 1-(3,4-dimethylphenyl)piperazine; mp 126°–127° C.

Elemental Analysis calculated for $C_{19}H_{23}FN_4$: C: 69.91, H: 7.10, N: 17.16. Found: C: 69.80, H: 7.09, N: 17.09.

EXAMPLE 7

6-[4-(3,4-Dichlorophenyl)piperazin-1-ylmethyl]-1,2,3,4-tetrahydroquinoxaline

Example 7 was prepared according to Example 2 except that in Step A 1-(3,4-dichlorophenyl)piperazine is substituted for 1-(3,4-dimethylphenyl)piperazine; mp 139°–141° C.

Elemental Analysis calculated for $C_{19}H_{22}Cl_2N_4$: C: 60.48, H: 5.88, N: 14.85. Found: C: 60.00, H: 6.06, N: 14.80.

EXAMPLE 8

6-(4-p-Tolylpiperazin-1-ylmethyl)-1,2,3,4-tetrahydroquinoxaline

Example 8 was prepared according to Example 2 except that in Step A 1-(p-tolyl)piperazine is substituted for 1-(3,4-dimethylphenyl)piperazine; mp 143°–145° C.

Elemental Analysis calculated for $C_{20}H_{2}N_4$: C: 74.50, H: 8.13, N: 17.37. Found: C: 74.19, H: 8.22, N: 17.34.

EXAMPLE 9

6-(4-m-Tolylpiperazin-1-ylmethyl)-1,2,3,4-tetrahydroquinoxaline

Example 9 was prepared according to Example 2 except that in Step A 1-(m-tolyl)piperazine is substituted for 1-(3,4-dimethylphenyl)piperazine; mp 135°–136° C.

Elemental Analysis calculated for $C_{20}H_{26}N_4$: C: 74.50, H: 8.13, N: 17.37. Found: C: 74.24, H: 7.91, N: 17.12.

EXAMPLE 10

6-[4-(4-Methylpyridin-2-yl)piperazin-1-ylmethyl]-1,2,3,4-tetrahydroquinoxaline

Example 10 was prepared according to Example 2 except that in Step A 1-(4-methylpyridin-2-yl)piperazine is substituted for 1-(3,4-dimethylphenyl)piperazine; mp 179°–180° C.

Elemental Analysis calculated for $C_{19}H_{25}N_5$: C: 70.56, H: 7.79, N: 21.65. Found: C: 70.36, H: 7.95, N: 21.56.

EXAMPLE 11

6-[4-(3-Trifluoromethylphenyl)piperazin-1-ylmethyl]-1,2,3,4-tetrahydroquinoxaline Example 11 was prepared according to Example 2 except that in Step A 1-(3-trifluoromethylphenyl)piperazine is substituted for 1-(3,4-dimethylphenyl)piperazine; mp 88°–91° C.

Elemental Analysis calculated for $C_{20}H_{23}F_3N_4$: C: 63.82, H: 6.16, N: 14.88. Found: C: 63.60, H: 6.25, N: 14.66.

EXAMPLE 12

6-(4-o-Tolylpiperazin-1-ylmethyl)-1,2,3,4-tetrahydroquinoxaline

Example 12 was prepared according to Example 2 except that in Step A 1-(o-tolyl)piperazine is substituted for 1-(3,4-dimethylphenyl)piperazine; mp 183°–185° C.

Elemental Analysis calculated for $C_{20}H_{26}N_4 \cdot 2.4$ HCl:
C: 55.92, H: 7.13, N: 13.04, Cl: 19.81. Found: C: 55.92, H: 7.26, N: 12.96, Cl: 19.74.

EXAMPLE 13

6-[4-(3-Chlorophenyl)piperazin-1-ylmethyl]-1,2,3,4-tetrahydroquinoxaline

Example 13 was prepared according to Example 2 except that in Step A 1-(3-chlorophenyl)piperazine is substituted for 1-(3,4-dimethylphenyl)piperazine.

Elemental Analysis calculated for $C_{19}H_{23}N_4Cl \times 1.5$ HCl $\times$ 0.2 $H_2O$:
C: 52.63, H: 6.63, N: 12.92, Cl: 20.44. Found: C: 52.80, H: 6.47, N: 12.91.

EXAMPLE 14

6-[4-(2-Chlorophenyl)piperazin-1-ylmethyl]-1,2,3,4-tetrahydroquinoxaline

Example 14 was prepared according to Example 2 except that in Step A 1-(2-chlorophenyl)piperazine is substituted for 1-(3,4-dimethylphenyl)piperazine.

Elemental Analysis calculated for $C_{19}H_{23}N_4Cl \times 2.05$ HCl$\times 0.1$ $H_2O$:
C: 52.39, H: 6.26, N: 12.86, Cl: 24.82. Found: C: 52.38, H: 6.36, N: 12.52, Cl: 24.90.

EXAMPLE 15

6-[4-(3,4-Dimethylphenyl)piperidin-1-ylmethyl]-1,2,3,4-tetrahydroquinoxaline

Example 15 was prepared according to Example 2 except that in Step A 1-(3,4-dimethylphenyl)piperidine is substituted for 1-(3,4-dimethylphenyl)piperazine; mp 185°–190° C.

Elemental Analysis calculated for $C_{22}H_{29}N_3 \cdot 2$ $HCl \cdot H_2O$:
C: 61.97, H: 7.80, N: 9.85, Cl:16.63. Found: C: 62.09, H: 7.86, N: 9.67, Cl: 17.08.

Biological Methods

Compounds were tested for their ability to bind to dopamine (DA) receptors as measured by their inhibition of [$^3$H]spiperone binding to the human D2, and D4.2 receptors (Pugsley, et al., 1995). The ability of test compounds to block the stimulation of [$^3$H]thymidine uptake in CHO pro-5 cells transfected with human DA D4.2 receptor cDNA caused by the DA agonist quinpirole was employed as an in vitro measure of DA receptor antagonist activity (Pugsley, et al., 1995). The effects of compounds on synthesis rates of rat brain catecholamines were estimated by measuring the accumulation of [3-(3,4-dihydroxyphenyl)-L-alanine (DOPA) after administration of the L-aromatic amino acid decarboxylase inhibitor, NSD 1015 (Pugsley, et al., 1995).

Pugsley T. A., Davis M. D., Akunne H. C., MacKenzie R. G., Shih Y.-H., Damsma G., Wikstrom H., Whetzel S. Z., Georgic L. M., Cooke L. W., DeMattos S. B., Corbin A. E., Glase S. A., Wise L. D., Dijkstra D., Heffner T. G., Neurochemical and Functional Characterization of the Preferentially Selective Dopamine D3 Agonist PD 128907. *J. Pharmacol. Exp. Ther.*, 1995;275:1355–1366.

Cell Lines Expressing Dopamine Receptor Isoforms

A cell line expressing human dopamine D2 (Long form) receptors was purchased from Oregon Health Sciences University, Portland, Oreg. The D2 receptor cDNA was subcloned into an expression vector, pRc/CMV. The plasmids were transfected by electroporation into CHO K1 cells. A single stable transfectant, resistant to the antibiotic 418, was isolated and selected for use in the binding studies. For D4 binding, CHO K1 cells stably transfected to express the human recombinant dopamine D4.2 receptor subtype, as described by Shih, et al., "The expression and functional characterization of human dopamine D4.2 receptor in CHO K1 cells," *Soc. Neurosci.*, 1995;21(Part 1):621.

Cell Culture and Preparation of Cell Membranes

CHO K1 cells expressing either human D2 and D4.2 receptors were grown in 162 cm$^2$ culture flasks in F12 medium (Gibco Laboratories, Grand Island, N.Y.) supplemented with 10% fetal bovine serum (FBS, Hyclone, Logan, Utah) in an atmosphere of 5% $CO_2$/95% air at 37° C. Cells were grown until confluent, after which growth medium was removed and replaced with 0.02% ethylene diamine tetracetate (EDTA) in a phosphate-buffered saline solution (Sigma Chemical Co., St. Louis, Mo.) and scraped from the flasks. The cells were centrifuged at about 1000×g for 10 minutes at 40° C. and then resuspended in TEM buffer (25 mM Tris-HCl, pH 7.4, 5 mM EDTA, and 6 mM $MgCl_2$) for D2 or the D4.2 buffer (50 mM Tris-HCl, pH 7.4, 5 mM EDTA, 1.5 mM $CaCl_2$, 5 mM KCl, and 120 mM NaCl) and homogenized. The membranes were pelleted by centrifugation at 20,000×g at 40° C. for 20 minutes. Then the pellets were resuspended in appropriate buffer at 1 mL/flask and stored at −70° C. until used in the receptor binding assay.

Receptor Binding Assays: D2,D4.2 Dopamine Receptors

A cell membrane preparation (400L) was incubated in triplicate with 50L[$^3$H]spiperone (0.2 nM for D2, 0.2 nM for D4.2), 50L buffer, or competing drugs where appropriate to give a final volume of 0.5 mL. After 60 minutes incubation at 25° C., the incubations were terminated by rapid filtration through Whatmann F/B lass fibre filters (soaked for 1 hour in 0.5% polyethylenimine) on a cell harvester, with three washes of 1 mL ice-cold buffer. Individual filter disks containing the bound ligand were placed in counting vials with 4 mL of scintillation fluid (Ready Gel, Beckman Instrument Inc., Fullerton, Calif.) and then counted in a Beckman LS-6800 liquid scintillation counter at an efficiency of 45%. Nonspecific binding was defined in presence of 1 mM of haloperidol.

[$^3$H]Thymidine Uptake Assay

The effects of test compounds on [$^3$H]thymidine uptake were carried out essentially as described by Pugsley, et al., 1995. CHO p-5 cells transfected with human D4.2 cDNA were seeded into 96-well plates at a density of about 5000 cells/well and were grown at 37° C. in a minimum essential medium (aMEM, Gibco) with 10% calf serum for 2 days. The wells were then rinsed three times with serum-free media. Fresh media (90 mL) was added along with 10 mL of test compound in water or vehicle alone. Eight wells of each plate received 100 mL of aMEM with 10% fetal calf serum. After culture for 16 to 17 hours, [3H]thymidine (1 mCi/well) was added for 4 hours. The cells were trypsinized and harvested onto filter mats with a 96-well Brandel cell harvester. The filters were counted in a Beta-Plate scintillation counter.

Dopamine Synthesis

Test compounds were administered to rats i.p. 30 minutes before the injection of the L-aromatic amino acid decarboxylase inhibitor, NSD 1015 (100 mg/kg i.p.). Rats were sacrificed by decapitation 30 minutes later. The striatum and mesolimbic regions were rapidly dissected from the brains and stored at −70° C. until assayed. Synthesis rates of rat brain catecholamines were estimated by measuring the accumulation of the DA precursor DOPA after NSD 1015 administration by HPLC with electrochemical detection (Puglsey, et al., 1995). Each value represents the mean of four determinations and is expressed as a percent of the control values.

Data Calculation

Saturation and competition binding data were analyzed using an iterative nonlinear least-square curve-fitting Ligand program. In competition experiments, apparent $K_i$ values were calculated from $IC_{50}$ values by method of Cheng and Prusoff, "Relationship between the inhibition constant ($K_i$) and the concentration of inhibitor which causes 50% inhibition ($IC_{50}$) of an enzymatic reaction," *Biochem. Pharmacol.*, 1973;22:3099–3108. Experimental compounds were made up as stock solutions in dimethyl sulfoxide (DMSO). The final concentration of 0.1% DMSO used in the incubation mixture had no effect on the specific binding. Each observation was carried out in triplicate. To allow these calculations, $K_i$ values were measured for the interaction of various ligands with the receptor. These were: [$^3$H]spiperone binding, human D2, 0.116+0.01 and human D4.2, 0.093+ 0.005 nM (n=3). The test results are presented below.

| Example Number | D4 $IC_{50}$, nM | D2 $IC_{50}$, nM | DA Synthesis in Rat Hippocampus | DA Synthesis in Rat Striatum | [$^3$H]thymidine $IC_{50}$, nM |
| --- | --- | --- | --- | --- | --- |
| 1 | 3.9 | 1809 | +62 | −9 | 10.0 |
| 2 | 2.8 | 2941 | +52 | +66 | 1.6 |
| 3 | 50 | 3200 | | | |
| 4 | 39.3 | | | | |
| 5 | 6.0 | 5882 | | +20 | 19 |
| 6 | 50.6 | | | | |
| 7 | 5.0 | 1650 | | +23 | |
| 8 | 11.1 | 5882 | | +39 | 8.2 |
| 9 | 36.3 | | | | |
| 10 | 35 | 5882 | | | |
| 11 | 22 | 683 | | | |

PROTOCOL FOR THE BEHAVIORAL ACTIVITY ASSESSMENT OF MICE AND RATS IN THE OMNITECH DIGISCAN ANIMAL ACTIVITY MONITORS

OBJECTIVE

The purpose of this test is to evaluate compounds for antipsychotic-like central nervous system (CNS) effects and a variety of other behavioral effects generally associated with CNS activity. This test has the capacity to determine drug effects on many aspects of locomotor activity in rodents, including horizontal activity (beam breaks), total distance traveled (in cm), number of movements, movement time (in sec), rest time (in sec), vertical activity (beam breaks), number of vertical movements, vertical time (in sec), stereotypy counts, number of stereotypic episodes, stereotypy time (in sec), margin and center time (in sec), clockwise and counterclockwise revolutions, and time (in sec) spent in each corner of the activity monitor. Generally, however, drug effects on behavior are assessed using total distance traveled (in cm) as the most accurate measure of locomotor activity.

METHODS

Animals and Drug Preparation

Male CD-1 albino mice weighing 20 to 40 g (Charles River Laboratories) or male Sprague-Dawley rats weighing 150 to 300 g (Harlan Laboratories) are used for these studies. Compounds are dissolved or suspended in physiological saline, occasionally requiring the addition of a few drops of 1N HCl and/or the surfactant, Emulphor®, to facilitate dissolution. Suspensions are placed on an ultrasonicator for up to 3 minutes, until the compound appears to have dissolved. Drug doses are expressed as the active moiety (taking into account the salt vs free base molecular weight of the drug). Test compounds are administered to mice in a volume of 10 mL/kg (IP, PO, or SC), or to rats in volumes of 5 mL/kg (IP, PO, or SC), 2 mL/kg (SC), or 1 mL/kg (IV). Drug administration can occur either 0, 30, or 60 minutes prior to measurement of activity levels, depending on the route of administration. Animals dosed PO are fasted overnight (16–20 hours) prior to dosing, while all animals have access to water up to the moment of dosing.

Procedure

The Omnitech Digiscan animal activity monitor consists of a 16"×16"×12" plexiglas cubicle enclosed inside 2 sets of 16 infrared photobeam sensors spaced 1 inch apart on all four sides of the bottom of the cubicle. An additional set of photobeam sensors are placed directly above the lower photobeam sensors, which measure vertical activity. Interruption of any beam should generate a flash of the LED indicator located in the center of the monitor mainframe. A diagnostic test of each of the 24 monitors is generally performed prior to the start of an experiment, in which all the photobeams are checked for any interruption. Each activity monitor can be divided into four 8" square quadrants using a plexiglas insert that fits inside the plexiglas cubicle, of which 2 quadrants (front left and rear right) can be used for activity testing. Generally, this divided arrangement is utilized for mouse activity studies (2 mice per divided monitor) as opposed to rat studies (1 rat per undivided monitor). Up to 999 data samples can be taken for up to 999 minutes duration. Generally, 6 data samples of 10-minute duration each are collected for mice (1-hour test), or 6 samples of 5-minute duration for rats (30-minute test).

Once the animal is placed in the activity chamber, the chambers are individually activated to begin collecting data. Activity levels are generally monitored with the overhead lights turned off, as the dark-stimulation tends to produce less variation in the data. The following types of data (with brief definitions) are collected during each experiment:

Variable 5: Horizontal activity—total number of beam interruptions that occurred in the horizontal sensor.

Variable 6: Total distance (in cm) traveled—a more accurate indicator of ambulatory activity as it takes into account any diagonal movement.

Variable 7: Number of movements—number of discrete movements separated by at least 1 second.

Variable 8: Movement time (sec)—amount of time in ambulation.

Variable 9: Rest time (sec)—difference between sample time and time spent moving.

Variable 10: Vertical activity—total number of beam interruptions that occurred in the vertical sensor as the animal rears up.

Variable 11: Number of vertical movements—each time the animal rears up and interrupts the vertical sensor (separated by at least 1 second).

Variable 12: Vertical time (sec)—time spent interrupting the vertical beams during rearing.

Variable 13: Stereotypy counts—number of beam breaks that occur during a period of repeated interruption (stereotypy) of the same beam (or set of beams).

Variable 14: Number of stereotypy—number of times the monitor observes stereotypic behavior, separated by at least 1 second.

Variable 15: Stereotypy time (sec)—total amount of time that stereotypic behavior is exhibited.

Variable 16: Clockwise revolutions—number of times the animal circles with at least a 2" diameter (will not pick up tighter rotating movements).

Variable 17: Anticlockwise revolutions—number of times the animal circles with at least a 2" diameter.

Variable 18: Margin time (sec)—time spent by the animal in close proximity (within 1 cm) to the walls of the plexiglas cage.

Variable 19: Center time (sec)—time spent by the animal away from the walls of the cage.

Variables 20, 21, 22, and 23: Time spent in corners (left and right front, left and right rear)—time spent by the animal in close proximity to two adjoining walls of the cage.

DATA ANALYSIS

Data can be expressed as either actual counts, time (in sec), centimeters traveled, or percent inhibition of activity relative to vehicle-treated control animals tested concurrently. Significant changes in activity (i.e., cm traveled), relative to controls, are determined by t-test or analysis of variance and Newman-Keul's multiple-range test. Stimulation of activity levels is indicated by negative values. The dose which could be expected to decrease activity levels by 50% ($ED_{50}$) and the 95% confidence limits (CL) around that value are estimated by regression analysis using at least three data points which fall on the linear portion of the dose-effect curve.

PROTOCOL FOR THE BLOCKADE OF AMPHETAMINE-STIMULATED LOCOMOTION IN RATS

The blockade of amphetamine-stimulated locomotion procedure is a modification of the Locomotor Activity Protocol in the Omnitech Digiscan Activity Monitors described above. The blockade of amphetamine-stimulated locomotion procedure uses the central nervous system stimulant d-amphetamine to assess antipsychotic activity of dopaminergic agents.

METHOD

Male Sprague-Dawley rats (Harlan Labs) were used for these studies. Drugs were dissolved in saline or water, and administered either orally (PO) or intraperitoneally (IP) in volumes of 5 mL/kg. Saline control rats and amphetamine (0.5 mg/kg IP) control rats are included with each study (n=4–6 rats per treatment group). For the IP studies, amphetamine is given 20 minutes prior to the drug, after which a 30 minute locomotor activity test is conducted. For the oral study, drug is dosed 30 minutes prior to the test, while amphetamine is given 15 minutes prior to the test, which allows time for oral absorption. Locomotor activity (centimeters travelled per 30 minute test) is measured in 16"×16" open chambers. Amphetamine generally produces a 2- to 3-fold increase in locomotion over saline controls. Drug effects are reported as percent reversal of amphetamine-stimulated locomotion. Significant changes in amphetamine-stimulated locomotion, relative to amphetamine treated controls, were determined by t-test. The dose which would reverse amphetamine-stimulated locomotion by 50% ($ED_{50}$) and the 95% confidence limits were estimated by regression analysis.

RESULTS

The compound of Example 7 produced a 100% blockade of amphetamine-stimulated locomotion at 30 mg/kg PO.

The compound of Example 1 produced a dose-dependent blockade of amphetamine-stimulated locomotion at 3, 10, and 30 mg/kg IP. Therefore, the IP blockade of amphetamine-stimulated locomotion $ED_{50}$=9.1 mg/kg.

The oral blockade of amphetamine-stimulated locomotion activity was >30 mg/kg.

The compound of Example 2 produced a dose-dependent decrease in the Omnitech Digiscan Activity Monitor test at 1, 3, 10, 30 mg/kg IP. Therefore, the locomotor activity had a $ED_{50}$=16.5 mg/kg IP.

In the blockade of amphetamine-stimulated locomotion test, the compound of Example 2 showed a dose-dependent blockade of amphetamine-stimulated locomotion at 1, 3, 10 and 30 mg/kg IP, resulting in an IP $ED_{50}$ of 3 mg.

When orally dosed (PO) an $ED_{50}$ of 5.8 mg/kg was seen. Moreover, IP administration of Example 2 produced significant blockade of apomorphine-induced disruption of prepulse inhibition in the Acoustic Startle test at 30 mg/kg IP.

PROTOCOL FOR THE PREPULSE INHIBITION OF ACOUSTIC STARTLE MODEL IN RATS

OBJECTIVE

Prepulse inhibition (PPI) of acoustic startle is a form of sensorimotor gating which occurs when a weak stimulus precedes a startling stimulus, resulting in diminution of the startle response amplitude. Schizophrenic patients exhibit reduced prepulse inhibition of acoustic startle compared to control subjects, consistent with a loss of sensorimotor gating. Thus, an animal model utilizing this phenomenon would be quite useful in the study of known and potential antipsychotic agents.

In rats, PPI can be blocked with direct dopamine (DA) agonists such as apomorphine, or the indirect DA agonist amphetamine, and this effect can be antagonized with dopamine antagonists such as haloperidol. This indicates a possible role of DA D2-like receptor stimulation in reducing sensorimotor gating in the rat. In addition to haloperidol and other D2 antagonist antipsychotic agents, the disruption of PPI produced by apomorphine can be blocked with the atypical DA D4/D2 antagonist clozapine.

METHODS

Animals and Drug Preparation

Male Sprague-Dawley rats from Harlan Labs (180–280 g) were housed in groups of five rats per cage and maintained on a 12-hour light/dark cycle with free access to food pellets and water. Testing occurred during the light phase between 0900 and 1700 hours. Test compounds were dissolved in saline with a few drops of either acetic acid (haloperidol) or 1N HCl (clozapine) and Emulphor® (a surfactant), and the pH adjusted to 5.5. Dosages represent the active moieties and were given in volumes of 5 mL/kg intraperitoneal (IP) 30 minutes prior to apomorphine. Apomorphine was dissolved in physiological saline and administered subcutaneously (SC) in a volume of 2 mL/kg immediately prior to the acoustic startle test. The number of animals per treatment are shown in the figures. Animals were not fasted and had free access to water prior to being transported to the test room.

Acoustic Startle Apparatus

Eight startle chambers (SR-LAB, San Diego Instruments) were used, each consisting of a Plexiglas cylinder resting on a Plexiglas frame within a ventilated sound-attenuating enclosure. Acoustic stimuli were presented via a loudspeaker mounted above the rat. A piezoelectric device was mounted below the Plexiglas frame, which detects and transduces the motion occurring inside the cylinder during the 100 msec after the onset of the startling stimulus. The average responses during the 100 msec record window (100×1 msec readings) were recorded by microcomputer and interface assembly (San Diego Instruments). Each of the eight chambers were calibrated to one another to ensure consistent levels of loudspeaker performance over a wide range of decibel (dB) levels (67 to 125 dB). Sound levels were assessed with a Radio Shack dB meter. Each stabilimeter (which houses the piezoelectric device) was adjusted to produce equal response sensitivity to a constantly vibrating calibrator.

PROCEDURE

Each animal was pretreated with saline or a dose of either haloperidol (0.01, 0.03, 0.1, 0.3, or 1.0 mg/kg IP 30 minutes prior to test) or clozapine (5, 10, 15, or 20 mg/kg IP 30 minutes prior to test) and singly housed in a holding rack adjacent to the test room. Apomorphine HCl (0.25 mg/kg) was injected SC immediately prior to test.

The test session in all experiments consisted of a total of 90 trials after a 5-minute test acclimation period of 70 dB white noise. The test session lasts a total of 30 minutes; several sequential tests are done to obtain an adequate number of rats per treatment group. The first and last 10 trials are 120 dB pulse-alone trials presented 7 to 23 seconds apart, during which time the rats habituate rapidly to the noise bursts. These data were not included in the PPI calculation. The middle 70 trials consisted of twenty 120 dB pulse-alone trials and 10 trials of each of the following five trial types in pseudorandom order: (1) no stim, (2) 72 dB prepulse 100 msec prior to 120 dB startle, (3) 74 dB prepulse 100 msec prior to 120 dB startle, (4) 78 dB prepulse 100 msec prior to 120 dB startle, and (5) 86 dB prepulse 100 msec prior to 120 dB startle. The prepulses (2, 4, 8, and 16 dB over 70 dB background noise) were of 20-msec duration, while the startle stimuli were 40-msec duration. When the prepulse was paired with the 120 dB pulse, no obvious acoustic difference could be detected by the human ear as compared to the 120 dB pulse alone.

DATA ANALYSIS

Prepulse inhibition of the acoustic startle reflex was expressed as the percent inhibition of the 120 dB startle amplitude produced when a 2 to 16 dB (over background) prepulse precedes the startling stimulus. Although data at 4 different prepulse levels was collected (2, 4, 8, and 16 dB prepulses), only the PPI for the 16 dB prepulse was shown in this report. Historical data has indicated that the drug effects were clearest at the highest prepulse level (i.e., lower prepulse levels tend to produce lower PPI, and DA antagonist effects are less pronounced at the lower prepulse levels). PPI was calculated for each individual animal in each treatment group as follows: [120 dB startle amplitude−(16 dB prepulse+120 dB startle amplitude)/120 dB startle amplitude]×100%. The prepulse inhibition values for each rat in each group were subjected to t-test (grouped data) and/or analysis of variance and Newman Keul's multiple range test to determine levels of significance at $p < 0.05$ or 0.01.

What is claimed is:

1. A compound having the Formula I wherein
each R is independently hydrogen or $C_1$–$C_6$ alkyl;
n is 1 to 5;
X is N or CH;
$R^1$ is aryl, substituted aryl, heteroaryl or substituted heteroaryl; and
$R_2$ is halogen, $C_1$–$C_6$alkyl, —OH, —$NO_2$, —$CF_3$, —CN, —$CO_2R$, or —COR and the pharmaceutically acceptable salts, esters, amides, and prodrugs thereof.

2. A compound in accordance with claim 1 wherein each R is hydrogen.

3. A compound in accordance with claim 1 wherein n is 1.

4. A compound in accordance with claim 1 wherein X is N.

5. A compound in accordance with claim 1 wherein X is CH.

6. A compound in accordance with claim 1 wherein $R^1$ is phenyl or substituted phenyl.

7. A compound in accordance with claim 6 wherein $R_1$ is substituted phenyl and the substituents are selected from halogen, $C_1$–$C_6$ alkyl, —OH, —$CF_3$, —$NO_2$, —CN, —$CO_2R$, or —COR.

8. A compound in accordance with claim 1 wherein $R^1$ is substituted heteroaryl.

9. A compound in accordance with claim 8 wherein the substituted heteroaryl is substituted pyridyl.

10. A compound in accordance with claim 1 wherein each R is hydrogen, n is 1, $R^2$ is hydrogen, X is N, and R is aryl, substituted aryl, heteroaryl, or substituted heteroaryl.

11. The compounds:
6-[4-(3-Chloro-4-methylphenyl)piperazin-1-ylmethyl]1,2,3,4-tetrahydroquinoxaline;
6-[4-(3,4-Dimethylphenyl)piperazin-1-ylmethyl]1,2,3,4-tetrahydroquinoxaline;
6-(4-Phenylpiperazin-1-ylmethyl)1,2,3,4-tetrahydroquinoxaline;
6-[4-(4-Methoxyphenyl)piperazin-1-ylmethyl]1,2,3,4-tetrahydroquinoxaline;
6-[4-(4-Chlorophenyl)piperazin-1-ylmethyl]1,2,3,4-tetrahydroquinoxaline;
6-[4-(4-Fluorophenyl)piperazin-1-ylmethyl]1,2,3,4-tetrahydroquinoxaline;
6-[4-(3,4-Dichlorophenyl)piperazin-1-ylmethyl]1,2,3,4-tetrahydroquinoxaline;
6-(4-p-Tolylpiperazin-1-ylmethyl)1,2,3,4-tetrahydroquinoxaline;

6-(4-m-Tolylpiperazin-1-ylmethyl)1,2,3,4-tetrahydroquinoxaline;

6-[4-(4-Methylpyridin-2-yl)piperazin-1-ylmethyl]1,2,3,4-tetrahydroquinoxaline;

6-[4-(3-Trifluoromethylphenyl)piperazin-1-ylmethyl]1,2,3,4-tetrahydroquinoxaline;

6-(4-o-Tolylpiperazin-1-ylmethyl)1,2,3,4-tetrahydroquinoxaline;

6-[4-(3-Chlorophenyl)piperazin-1-ylmethyl]1,2,3,4-tetrahydroquinoxaline;

6-[4-(2-Chlorophenyl)piperazin-1-ylmethyl]1,2,3,4-tetrahydroquinoxaline; or

6-[4-(3,4-Dimethylphenyl)piperidin-1-ylmethyl]1,2,3,4-tetrahydroquinoxaline.

12. A method of treating psychosis, the method comprising administering to a patient having psychosis a therapeutically effective amount of a compound of claim 1.

13. A method of treating schizophrenia, the method comprising administering to a patient having schizophrenia a therapeutically effective amount of a compound of claim 1.

14. A method of inhibiting dopamine D4 receptors, the method comprising administering to a patient in need of dopamine D4 receptor inhibition an inhibiting amount of a compound of claim 1.

15. A pharmaceutically acceptable composition, the composition comprising a compound of claim 1.

* * * * *